United States Patent [19]

Sipos

[11] Patent Number: 4,473,547

[45] Date of Patent: Sep. 25, 1984

[54] ANTICARIES COMPOSITIONS

[75] Inventor: Tibor Sipos, Lebanon, N.J.

[73] Assignee: Johnson & Johnson Products Inc., New Brunswick, N.J.

[21] Appl. No.: 442,696

[22] Filed: Nov. 18, 1982

[51] Int. Cl.³ .................... A61K 7/16; A61K 7/18
[52] U.S. Cl. .................................... 424/52; 424/49
[58] Field of Search ............................ 424/49-58

[56] References Cited

U.S. PATENT DOCUMENTS

| | | | |
|---|---|---|---|
| 4,138,477 | 2/1979 | Gaffar | 424/56 |
| 4,243,658 | 1/1981 | Chang | 424/49 |
| 4,304,766 | 12/1981 | Chang | 424/52 |
| 4,307,077 | 12/1981 | Buck | 424/56 |
| 4,307,078 | 12/1981 | Buck | 424/56 |
| 4,314,991 | 2/1982 | Sipos | 424/56 |
| 4,360,512 | 11/1982 | Vidra | 424/56 |
| 4,360,513 | 11/1982 | Buck | 424/56 |
| 4,360,515 | 11/1982 | Buck | 424/56 |
| 4,362,712 | 12/1981 | Buck | 424/49 |
| 4,364,927 | 12/1982 | Sipos et al. | 424/56 |

OTHER PUBLICATIONS

A.D.A. Accepted Dental Therapeutics 38th Ed., Sep. 1979, American Dental Assn., Chicago, Ill., pp. 316-338, "Fluoride Compounds."

Primary Examiner—Shep K. Rose
Attorney, Agent, or Firm—Steven P. Berman

[57] ABSTRACT

Compositions providing improved protection against dental caries consisting of a pharmaceutically acceptable fluoride compound and a pharmaceutically acceptable sulfonated polymeric material in a suitable vehicle are described.

6 Claims, No Drawings

ANTICARIES COMPOSITIONS

BACKGROUND OF THE INVENTION

The present invention relates to compositions for preventing dental caries. More particularly, it relates to fluoride-containing compositions that have enhanced activity in preventing dental caries.

The use of soluble fluoride salts, such as stannous fluoride and sodium fluoride, to reduce the incidence of dental caries in the general population is a well-known and ongoing endeavor. The administration of these fluoride compounds takes many forms, including the fluoridation of drinking water, professional treatment by dentists and incorporation in oral hygiene compositions such as dentifrices and mouthrinses.

Notwithstanding the widespread acceptance of such compositions, there is an ongoing search for more effective compositions and, therefore, there is a need to enhance the fluoride activity of various fluoride compounds by the addition of other compounds. In copending U.S. patent application Ser. No. 303,284, filed Sept. 17, 1981, now U.S. Pat. No. 4,396,599, there is suggested the use of various zinc salts to enhance the activity of fluoride compounds.

One of the objects of the present invention is to provide improved compositions for preventing dental caries.

Another object of this invention is to provide anticaries compositions comprising one or more anticaries compounds in combination with a compound which enhances the anticaries activity of said anticaries compounds. These and other objects of the invention will become apparent from the foregoing description.

SUMMARY OF THE INVENTION

In accordance with the present invention, there are provided compositions useful in preventing dental caries comprising (a) at least one fluoride salt and (b) a specific sulfonated polymeric material.

The enhancing effect on the anticaries properties of the compositions of the present invention is most notable when the fluoride salt is employed with the sulfonated polymeric material within specific concentrations and the compositions of the invention can be employed in various oral hygiene products.

DETAILED DESCRIPTION OF THE INVENTION

It has now been discovered that the rate of development of dental caries, as characterized by proximal, smooth surface, pit and fissure caries, can be prevented or substantially retarded by the daily application to the teeth of a composition comprising a pharmaceutically acceptable oral hygiene vehicle containing an effective concentration to prevent or inhibit dental caries of a pharmaceutically acceptable fluoride salt and a pharmaceutically acceptable sulfonated polymeric material.

Typical pharmaceutically acceptable fluoride compounds that are suitable for use in the compositions of this invention include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluroide and amine fluoride. The hydrophilic, polymeric sulfonates found useful in accordance with the present invention are essentially sulfonated derivatives of formaldehyde condensation polymers of certain aromatic compounds wherein the repeating unit of the polymer is selected from the group consisting of structure (A),

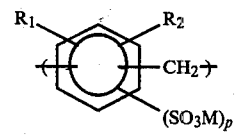

and structure (B),

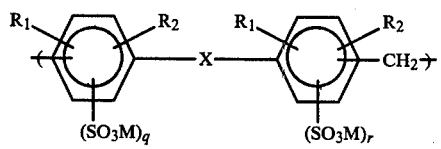

wherein $R_1$ and $R_2$ are each independently selected from the group consisting of hydrogen, linear or branched alkyl of from 8 to 20 carbon atoms, alkoxy of from 8 to 20 carbon atoms, fluorine, chlorine, and bromine, provided, however, that $R_1$ and $R_2$ cannot both be hydrogen, chlorine, fluorine or bromine; X is a linkage selected from the group consisting of a direct covalent bond between the aromatic rings, a lower alkylene of 1 to 5 carbon atoms, a lower alkylidene having 2 to 5 carbon atoms, oxygen, sulfur, and $O(CH_2)_nO$, where n is an integer from 2 to 20; p is from about 0.4 to about 1.2, (preferably about 1), the sum of q and r is between about 0.8 and about 2.4 (preferably from about 1 to about 2); and M is selected from the group consisting of lithium, sodium, potassium, calcium, magnesium, zinc, aluminum, copper, hydrogen, ammonium and substituted ammonium ions derived from pharmaceutically acceptable organic amines. The zinc salts are particularly preferred. In general, the metal and ammonium salts are preferred over the free sulfonic acid derivatives because of their higher water solubility and lower degree of acidity (closer to neutrality), thereby favoring their use in oral hygiene formulations.

The formaldehyde polymers that are sulfonated are preferably preferred by the acid catalyzed condensation of aqueous 37% formaldehyde or paraformaldehyde with selected aromatic compounds under standard conditions reported in the literature and reviewed extensively in the text by J. F. Walker, "Formaldehyde", R. E. Krieger Publishing Co., Third Edition, 1975. By selecting aromatic compounds of varied structure, condensation reactions with formaldehyde can afford a wide variety of aromatic/formaldehyde polymers, having generalized structure (I), wherein the unsulfonated aromatic moiety, Ar, corresponds to the aromatic structures in the repeating units of structures (A) and (B) of the sulfonated polymers defined above.

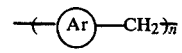

Typical examples of aromatic compounds which can be utilized for preparation of the formaldehyde polymers of general structure (I) are octylbenzene, nonylbenzene, dodecylbenzene, octadecylbenzene, and 1,12-bis(-phenoxy)dodecane.

As indicated in structures A and B, the exact position or orientation of the methylene ($—CH_2—$) linkages on the aromatic rings is not known and is generally recognized as being complex and varied. It is well understood that some of the formaldehyde linkages may not be solely of the —CH$_2$— type but can also involve some extended units, such as CH$_2$OCH$_2$ and CH$_2$(OCH$_2$)$_n$OCH$_2$, or other possibilities (cf. Walker, supra). However, despite these uncertainties, NMR data on the unsulfonated precursors as well as the sulfonated formaldehyde polymers indicated that the formaldehyde linkages consist essentially of the methylene linkage depicted in structures A and B. The molecular weights of the unsulfonated polymers were generally in the 2000–5000 molecular weight range, as established by viscosity-average and weight-average molecular weight (light scattering) measurements.

The formaldehyde polymers are prepared by heating approximately equimolar quantities of formaldehyde and the selected aromatic compound in an inert solvent, in the presence of an acid catalyst such as sulfuric acid, p-toluenesulfonic acid, methanesulfonic acid, or perchloric acid, for several hours. Depending on the nature of the formaldehyde polymer, the latter precipitates from the reaction mixture either directly on cooling to room temperature or upon quenching in water. The preferred solvent for the reaction is acetic acid, a solvent known to favor formation of polymers having oxygen-free linkages (Walker, supra, p. 439), such as those represented by structure (I).

The sulfonated formaldehyde polymers have a molecular weight of about 500 to 10,000, preferably about 2,000 to 5,000. They are substantially soluble in water or mixed solvents comprising water and an organic solvent miscible therewith (generally at least 1% w/w). The degree of sulfonation (D.S.), defined herein as the average number of sulfonate or sulfonic acid groups per repeat unit of the polymeric structure.

Preferred sulfonation agents for preparing the sulfonated polymeric barriers are anhydrous sulfur trioxide, triethyl phosphate (TEP) complexes of sulfur trioxide, and chlorosulfonic acid. Due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is found preferable to moderate the sulfonation reactivity by utilization of the sulfur trioxide complexes with triethyl phosphate (TEP), which minimize or essentially eliminate formation of crosslinked by-products [cf. A. F. Turbak, Ind. Eng. Chem., Prod. R & D, 1, 275(1962); U.S. Pat. No. 3,072,619 (Jan. 8, 1963); A. F. Turbak and A. Noshay, U.S. Pat. No. 3,206,492 (Sept. 14, 1964); N. H. Canter, U.S. Pat. No. 3,642,728 (Feb. 15, 1972); A. Noshay and L. M. Robeson, J. Applied Polymer Science, 20, 1885 (1976)]. In some instances where it is difficult to effect sulfonation under milder conditions with the complexes, sulfonation with sulfur trioxide (alone) or chlorosulfonic acid is more effective.

Sulfonations are effected in solvents such as methylene chloride, 1,2-dichloroethane, and chloroform, since these are generally good solvents for the starting aromatic polymer and poor solvents for the sulfonated polymer. In these instances where the product is soluble in the reaction medium and does not precipitate, the sulfonated polymer is isolated by removing the solvent and converted to well-defined solids by either trituration or slurrying with an appropriate non-solvent.

Temperature control of the sulfonation reaction with sulfur trioxide and its complexes with TEP is not very critical. Acceptable results are obtained over a temperature range of −20° C. to +40° C. range. Sulfonations are generally effected at ambient room temperatures, since the sulfonation exotherm is very mild and rarely results in temperature increases beyond 35° C.

Typical impurities in the sulfonated polymer are small amounts of unreacted polymer, excess sulfonation agent (as sulfuric acid), and residual triethyl phosphate which are occluded in the solid polymer. Substantial purification can be effected by slurrying the polymeric sulfonic acid derivatives in non-solvents therefor, such as the halocarbons. Removal of the free sulfuric acid is difficult, since it complexes strongly with the polymeric product. Diethyl ether is an exceptionally good complexing agent for sulfuric acid and effectively removed this contaminant when freshly isolated polymeric solids are slurried in the ether and filtered. Other effective additives for sulfuric acid removal are halocarbon solvent blends with diethyl ether and other oxygenated solvents, such as ethyl acetate and acetone. The sulfuric acid, if not removed, results in contamination of the metal salts with, e.g. sodium sulfate, in the case where the sodium sulfonate polymer is produced.

The preferred process for purification of the sulfonated polymers, particularly, highly water soluble types, is by dialysis in membrane tubes or hollow fiber dialyzing units having a molecular weight cut-off well below the molecular weight of the polymer. Dialysis removes all of the low molecular impurities, triethyl phosphate, and inorganic salts. High purity polymers are isolated as solids by freeze-drying or spray drying the dialyzed polymer solution.

The D.S. of the sulfonated polymers can be varied by adjusting the molar ratio of sulfonating agent to polymer. In preparing the sulfonated polymers of this invention, the exact position of sulfonation on the aromatic rings is not known with certainty, nor is it considered important in the practice of this invention. The D.S. of the formaldehyde polymers, either as their sulfonic acid or sulfonate salt derivatives, can be determined by any of several methods: (a) NMR analysis, (b) elemental analysis for sulfur to carbon ratio determination, (c) direct titration of the sulfonic acid derivative with standard sodium hydroxide to obtain the milliequivalents of sulfonic acid groups per gram of sample, value approximately equivalent to the ion-exchange capacity of the sulfonated polymer, or (d) atomic absorption assay for the metal content of carefully purified samples of the sulfonated salts.

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly and are collected, or they are isolated after solvent stripping. Purification of the sulfonate salt by dialysis is the preferred procedure for the more highly water soluble salts.

Multivalent metal salts, such as calcium, magnesium, zinc, copper, and aluminum salts, of the sulfonated polymers are prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions, as typified by the following equations, where P represents the polymer chain:

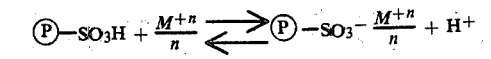

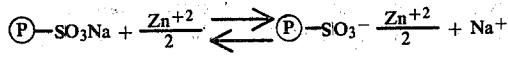

Ammonium salts of the sulfonic acid polymer can be prepared by direct addition of ammonia or a primary, secondary, or tertiary organic amine.

In connection with the above compositions, the fluoride ion concentration should be from about 0.005 to 2.00% by weight of the total composition, preferably from about 0.01 to 1.00% The concentration of the sulfonated polymeric material should be at least 0.0001% by weight of the total composition, preferably from about 0.01 to 5.00% and most preferably from about 0.05 to 3.00%. In concentrate formulations, the sulfonated polymeric material may have a concentration as high as 80% by weight of the total composition.

Suitable pharmaceutically acceptable oral hygiene vehicles, that may be used alone or in any compatible combination, include glycerol, water, ethanol, polyethylene glycol, propylene glycol and sorbitol. Alternatively, any pharmaceutically acceptable vehicle which is compatible with the sulfonated polymeric material and fluoride salts used may be employed.

The compositions of this invention may be in the form of a mouthrinse, dentifrice, gel, powder, solution, varnish, lozenge, chewing gum, slow release device or concentrate to be diluted or other form suitable for oral application. Any pharmaceutically acceptable materials, such as those ordinarily used in such oral compositions, that are compatible may be employed in the compositions of this invention.

In accordance with the present invention, the compositions are applied to the teeth with an appliance, e.g., toothbrush, swab, mechanical cleansing device, impregnated dental floss or the like, by gently brushing the teeth at least once daily, more preferably twice daily.

Specific embodiments of the anticaries compositions prepared in accordance with the present invention are illustrated by the following representative examples. It will be understood, however, that the invention is not confined to the specific limitations set forth in the individual examples, but rather to the scope of the appended claims.

EXAMPLE I

A gel dentifrice is prepared as follows: the Pluronic F-127 surface active agent is dissolved in 50 ml. of deionized water with continuous stirring at 70° C. The sulfonated 1-phenylnonane/formaldehyde polymer is then added with stirring until dissolved. The resultant solution is then cooled to 50° C. and the sodium fluoride, glycerol, sorbitol, sodium benzoate, sweetener, flavoring, dye and silicone dioxide are individually added. The pH of the solution is then adjusted to 5.5 to 6.0 with 1.0N HCl or 1.0N NaOH as required and deionized water is added to bring the total weight to 100 g. The solution is permitted to gel overnight at 15° C. The resulting gel dentifrice has the following composition:

|  | % w/w |
|---|---|
| sodium fluoride | 0.22 |
| zinc salt of a sulfonated 1-phenylnonane/formaldehyde polymer | 1.00 |
| silicon dioxide | 1.00 |
| Pluronic F-127 (Wyandotte Chemicals Corporation's tradename for a nonionic surface active agent prepared by the addition of ethylene oxide to polypropylene glycol) | 18.00 |
| sweetener | 0.80 |
| sodium benzoate | 0.30 |
| glycerol | 10.00 |
| sorbitol solution, 70% | 2.00 |
| flavoring | 0.80 |
| dye (0.5% aq. soln.) | 0.70 |
| deionized water | q.s. to 100 |

EXAMPLE II

An abrasive paste dentifrice is prepared as follows: the sodium fluoride, sodium benzoate, sweetener, Pluronic F87 and zinc salt of a sulfonated 1,12-bis(phenoxy)dodecane/formaldehyde polymer are dissolved in 25 ml. of water at 50° C. with continuous stirring. In separate vessels, the xanthan gum is mixed with the glycerol and the Natrosol 250H is mixed with the sorbitol and then each of these mixtures is added to the solution. The Zeothix 265, titanium dioxide, and hydrous silica gel are then individually added to the solution with stirring. The pH of the solution is then adjusted to 5.0 to 6.0 with 1.0N HCL or 1.0N NaOH as required and the flavoring is then added as well as enough deionized water to bring the solution to 100 g. The resultant product is mixed and placed in containers and permitted to stand at 20° C. overnight.

The resulting abrasive paste dentifrice has the following composition:

|  | % w/w |
|---|---|
| sodium fluoride | 0.22 |
| zinc salt of a sulfonated 1,12-bis(phenoxy)-dodecane/formaldehyde polymer | 1.00 |
| sodium benzoate | 0.20 |
| sweetener | 0.50 |
| titanium dioxide | 0.50 |
| flavoring | 1.00 |
| glycerol | 10.00 |
| sorbitol soln. 70% | 12.00 |
| hydrous silica gel | 15.00 |
| Zeothix 265 | 9.00 |
| Natrosol 250H (Hercules Inc. tradename for nonionic water soluble cellulose ether) | 1.00 |
| xanthan gum | 1.00 |
| Pluronic F87 (Wyandotte Chemical Corporation's tradename for a nonionic surface active agent prepared by the addition of ethylene oxide to polypropylene glycol) | 3.00 |
| deionized water | q.s. to 100 |

EXAMPLE III

A mouthrinse solution is prepared as follows: the flavoring is dissolved in ethanol in a suitable stainless steel vessel. The Pluronic F-108, water, glycerol, sorbitol, sweetener, zinc salt of a sulfonated 1,12-bis(phenoxy)dodecane/formaldehyde polymer and sodium fluoride are individually added with continuous stirring. The pH is adjusted to 5.5 to 6.0 with 1.0N HCl and the entire solution is strained through a 400 mesh stainless steel screen.

The resulting mouthrinse has the following composition:

|  | % w/w |
|---|---|
| sodium fluoride | 0.05 |
| zinc salt of a sulfonated 1-phenylnonane/ formaldehyde polymer | 0.02 |
| ethanol, USP | 7.0 |
| Pluronic F108 (Wyandotte Chemical Corporation's tradename for a nonionic surface active agent prepared by the addition of ethylene oxide to polypropylene glycol) | 2.00 |
| glycerol | 10.00 |
| sorbitol soln. 70% | 10.00 |
| sweetener | 0.20 |
| flavoring | 0.20 |
| deionized water | q.s. to 100 |

EXAMPLE IV

An in vitro assay technique is utilized to demonstrate the enhancing properties of the sulfonated polymeric material on fluoride ion activity. This technique is based on the titrametric measurement of organic acids produced from sucrose by the cariogenic bacterium *S. mutans*.

A fresh cell suspension of *Streptococcus mutans* 6715, grown in Trypticase Soy Broth for 16–18 hrs. at 35° C., centrifuged and the cells then resuspended in buffer containing dithiothreitol is used in the assay system. The cell suspension is stored under anaerobic conditions at 4° C. until used. The assay utilizes a pH-stat and the reaction is carried out under a nitrogen atmosphere at 37° C. The production of acid is monitored with the automatic addition of 0.005N potassium hydroxide solution. The cells are initially activated with glucose at pH 7.5. After the exhaustion of glucose, the pH of the reaction mixture is manually dropped to 5.5 with 0.01N HCl. Sucrose is added and after 4 minutes of acid production, the test compound is added. The rate of acid production is recorded as ml of potassium hydroxide consumed per minute to maintain a pH of 5.5 Antiacidogenic activity is reported as that amount of compound which reduces the acid production by a given percent as compared to a control containing no test compound. The higher the percent reduction of acid production of a composition containing the sulfonated polymeric material and fluoride ion compared to a composition containing the sulfonated polymeric material alone, the better the anticaries activity of such a composition. When the sulfonated sodium salt of a 1-phenylnonane/-formaldehyde polymer is tested at a concentration of 0.001 as above, the following results are obtained:

| % reduction of acid production | | |
|---|---|---|
| fluoride alone | compound alone | compound plus fluoride ion |
| 20 | 23 | 80 |

When disodium 1,12-bis(sulfophenoxy)dodecane/formaldehyde polymer is tested at a concentration of 0.002 as above, the following results are obtained:

| % reduction of acid production | | |
|---|---|---|
| fluoride alone | compound alone | compound plus fluoride ion |
| 20 | 39 | 82 |

In addition to the preferred embodiments described herein, other embodiments, arrangements, and variations within the spirit of the invention and the scope of the appended claims will occur to those skilled in the art.

What is claimed is:

1. In a composition for preventing dental caries consisting essentially of a pharmaceutically acceptable oral hygiene vehicle containing an effective concentration to prevent caries of at least one pharmaceutically acceptable fluoride salt; the improvement which consists of including therewith a fluoride ion activating enhancing amount of a pharmaceutically acceptable sulfonated polymeric material, said polymeric material having repeating units selected from the group consisting of structure (A),

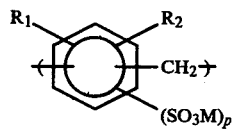

and structure (B),

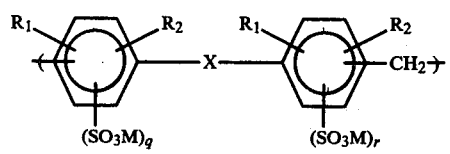

wherein $R_1$ and $R_2$ are each independently selected from the group consisting of hydrogen, linear or branched alkyl of from 8 to 20 carbon atoms, alkoxy of from 8 to 20 carbon atoms, fluorine, chlorine, and bromine, provided, however, that $R_1$ and $R_2$ cannot both be hydrogen, chlorine, fluorine or bromine; X is a linkage selected from the group consisting of a direct covalent bond between the aromatic rings, a lower alkylene of 1 to 5 carbon atoms, a lower alkylidene having 2 to 5 carbon atoms, oxygen, sulfur, and $O(CH_2)_nO$, where n is an integer from 2 to 20; p is from about 0.4 to about 1.2, the sum of q and r is between about 0.8 and about 2.4; and M is selected from the group consisting of lithium, sodium, potassium, calcium, magnesium, zinc, aluminum, copper, hydrogen, ammonium and substituted ammonion ions derived from pharmaceutically acceptable organic amines.

2. The composition of claim 1 wherein the sulfonated polymeric material is a salt of a sulfonated 1-phenylnonane/formaldehyde polymer.

3. The composition of claim 1 wherein the sulfonated polymeric material is a salt of a sulfonated 1,12-bis(-phenoxy)dodecane/formaldehyde polymer.

4. The composition of claim 1 wherein said fluoride salt is selected from the group consisting of sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

5. The composition of claim 1 wherein the fluoride ion is present in a concentration of from about 0.005 to 2.00% by weight of the total composition.

6. The composition of claim 1 wherein the sulfonated polymeric material is present in a amount of from about 0.0001 to 80.00% by weight of the total composition.

* * * * *